(12) United States Patent
Vazquez

(10) Patent No.: US 7,097,785 B2
(45) Date of Patent: Aug. 29, 2006

(54) FLUOROPOLYMER—AMINO TERMINATED POLYDIORGANOSILOXANE COMPOSITIONS FOR TEXTILE TREATMENTS

(75) Inventor: Fernando Vazquez, Greensboro, NC (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 11/080,588

(22) Filed: Mar. 15, 2005

(65) Prior Publication Data

US 2005/0224746 A1   Oct. 13, 2005

Related U.S. Application Data

(60) Provisional application No. 60/561,835, filed on Apr. 12, 2004.

(51) Int. Cl.
*D06M 15/643* (2006.01)
*D06M 15/00* (2006.01)

(52) U.S. Cl. .................. 252/8.62; 252/8.61; 252/8.63; 428/391; 442/80; 442/81

(58) Field of Classification Search ............... 252/8.61, 252/8.62, 8.63; 428/391; 442/80, 81
See application file for complete search history.

(56) References Cited

U.S. PATENT DOCUMENTS

| 4,101,272 A | 7/1978 | Guise et al. |
|---|---|---|
| 4,293,611 A | 10/1981 | Martin |
| 4,401,698 A | 8/1983 | Tripp |
| 4,781,844 A | 11/1988 | Kortmann et al. |
| 4,978,462 A | 12/1990 | Sheppard |
| 5,068,295 A | 11/1991 | Misaizu et al. |
| 5,247,008 A | 9/1993 | Michels et al. |
| 5,536,304 A | 7/1996 | Coppens et al. |
| 5,883,185 A | 3/1999 | Matsumura et al. |
| 6,171,515 B1 | 1/2001 | Evans et al. |
| 6,472,019 B1 | 10/2002 | Yamaguchi et al. |
| 6,475,568 B1 | 11/2002 | Czech |
| 6,582,620 B1 | 6/2003 | Miyadai et al. |
| 6,696,158 B1 * | 2/2004 | Chen et al. .................. 428/421 |
| 2004/0210074 A1 * | 10/2004 | Hupfield et al. ............ 556/413 |

FOREIGN PATENT DOCUMENTS

| GB | 0407433.2 | 4/2004 |
|---|---|---|
| WO | WO 02/068752 A2 | 9/2002 |

* cited by examiner

*Primary Examiner*—Anthony J. Green
(74) *Attorney, Agent, or Firm*—Alan Zombeck

(57) ABSTRACT

Treatment of textiles by a fluoropolymer-amino terminated polydiorganosiloxane composition is disclosed. The fluoropolymer-amino terminated polydiorganosiloxane compositions are prepared by combining a fluoropolymer and an amino terminated polydiorganosiloxane. The resulting compositions improve the hand or feel of the fabric without significantly diminishing oil repellency properties associated with fluoropolymers.

6 Claims, No Drawings

FLUOROPOLYMER—AMINO TERMINATED POLYDIORGANOSILOXANE COMPOSITIONS FOR TEXTILE TREATMENTS

CROSS REFERENCE

This application claims the benefit of U.S. Provisional Application No. 60/561,835, filed on Apr. 12, 2004.

FIELD OF THE INVENTION

This invention relates to the treatment of textiles by a fluoropolymer-amino terminated polydiorganosiloxane composition. The fluoropolymer-amino terminated polydiorganosiloxane compositions are prepared by combining a fluoropolymer and an amino terminated polydiorganosiloxane. The resulting compositions improve the hand or feel of the fabric without significantly diminishing oil repellency properties associated with fluoropolymers.

BACKGROUND OF THE INVENTION

Silicones are used as textile treatments to impart a variety of properties, but in particular are used for improving the feel or hand of treated fabrics. For example, reference may be had to U.S. Pat. No. 4,781,844 (Nov. 1, 1988), U.S. Pat. No. 4,978,462 (Dec. 18, 1960), and U.S. Pat. No. 6,171,515 (Jan. 9, 2001), for a description of the general state of the art. The '515 patent in particular provides a detailed overview on the use of various silicones in the textile industry.

Fluorocarbons are extensively used in the textile industry to impart water and oil repellency to fabrics. They are also used to provide soil release properties. However, one of the major drawbacks of fluorocarbon treatments is the harsh feel imparted to the fabric surface. The increasing use of fluoropolymers in apparel fabrics and garments demands a higher level of softness.

There have been several attempts to combine various fluorocarbons and silicones into a single textile treatment to offer the combined benefits of each. However, such attempts have usually resulted in comprising one or more fabric attributes. For example, the addition of a silicone to a fluorocarbon treatment composition may improve the hand of the fabric, but the oil repellency of the combined treatment is often much worse when compared to the fluorocarbon treated fabrics. Thus, there is a need to identify fluorocarbon based textile treating compositions that maintain the attributes associated with fluorocarbon treatments, but improve the deficiencies, such as poor hand.

The present inventor has discovered certain silicones, namely amino terminated polydiorganosiloxanes, when combined with fluoropolymers, provide textile treatments that provide the positive attributes of fluoropolymers, while providing improved hand of the treated fabrics.

SUMMARY OF THE INVENTION

The present invention provides a composition comprising;
A) a fluoropolymer, and
B) an amino terminated polydiorganosiloxane.

The invention further relates to a method of treating fibers or textiles comprising;
I) mixing,
A) a fluoropolymer,
B) an amino terminated polydiorganosiloxane, and
II) applying the product of step I on fibers or textiles.

DETAILED DESCRIPTION OF THE INVENTION

The present invention provides a composition comprising;
A) a fluoropolymer, and
B) an amino terminated polydiorganosiloxane.

Component A) is a fluoropolymer. The fluoropolymer can be any fluorocarbon polymer, either used neat, or alternatively in an emulsion form, that is known in the art for treating fibers, fabrics, or textiles. Typically, the fluoropolymer is selected from a fluoroalkyl acrylate copolymer, a fluorinated urethane, or a fluorinated ester. Emulsions of a fluoroalkyl acrylate copolymer, a fluorinated ester, or a fluorinated urethane can also be used.

A fluoroalkyl acrylate copolymer is illustrated by the formula shown below.

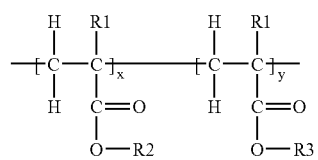

In the above structure, R1 is hydrogen or an alkyl group such as methyl; R2 represents a fluorocarbon group such as $-(CH_2)_m(CF_2)_nCF_3$; R3 represents an alkyl group such as $-(CH_2)_nCH_3$; m is 0–5; n is 2–19; and x and y have values dependent upon the desired chain length.

Emulsions containing fluoroalkyl acrylate copolymers are commercially available from companies such as Daikin Industries Ltd., Osaka, Japan, under the trade mark UNIDYNE™ TG-571 and Noveon Inc. Charlotte, N.C., under the trade mark UNIDYNE™ TG-532 Emulsions containing fluorinated urethanes are commercially available from companies such as E.I. DuPont de Nemours, Wilmington, Del., under their trademark ZONYL® 7910.

Component B) is an amino terminated polydiorganosiloxane. The amino terminated polydiorganosiloxane has the general formula, $A-(R_2SiO)_c-A$, where A represents an amino-functional hydrocarbon group, R is an alkyl or aryl group, and c is greater than zero, alternatively, 1–1000, alternatively 1–500, or alternatively 1–200.

The amino-functional hydrocarbon group, A, comprises at least one primary, secondary, or tertiary amine. Each amino-functional hydrocarbon group can contain a single amine, diamine, triamine, or polyamine. The alkyl groups, R, in the amino-functional hydrocarbon are illustrated by methyl, ethyl, propyl, butyl, hexyl, octyl, decyl, dodecyl, hexadecyl, and octadecyl, with the alkyl group typically being methyl. The aryl groups are illustrated by phenyl, naphthyl, benzyl, tolyl, xylyl, xenyl, methylphenyl, 2-phenylethyl, 2-phenyl-2-methylethyl, chlorophenyl, bromophenyl and fluorophenyl, with the aryl group typically being phenyl.

The amino-functional hydrocarbon group is illustrated by groups having the formula;

$-R^1NHR^2$, $-R^1NR_2^2$, or $-R^1NHR^1NHR^2$, wherein each $R^1$ is independently a dival hydrocarbon group having at least 2 carbon atoms, and $R^2$ is hydrogen or an alkyl group. Each $R^1$ is typically an alkylene group having from 2 to 20 carbon atoms. $R^1$ is illustrated by groups such as; $-CH_2CH_2-$, $-CH_2CH_2CH_2-$, $-CH_2CHCH_3-$, $-CH_2CH_2CH_2CH_2-$, $-CH_2CH(CH_3)CH_2-$, —CH$_2$CH$_2$CH$_2$CH$_2$CH$_2$—,
—CH$_2$CH$_2$CH$_2$CH$_2$CH$_2$CH$_2$—, —CH$_2$CH$_2$CH(CH$_2$CH$_3$)CH$_2$CH$_2$CH$_2$—, —CH$_2$CH$_2$CH$_2$CH$_2$CH$_2$CH$_2$CH$_2$CH$_2$—, and —CH$_2$CH$_2$CH$_2$CH$_2$CH$_2$CH$_2$CH$_2$CH$_2$CH$_2$—. The alkyl groups R$^2$ are as above for R. When R$^2$ is an alkyl group, it is typically methyl.

Some examples of suitable amino-functional hydrocarbon groups are; —CH$_2$CH$_2$NH$_2$, —CH$_2$CH$_2$CH$_2$NH$_2$, —CH$_2$CHCH$_3$NH, —CH$_2$CH$_2$CH$_2$CH$_2$NH$_2$, —CH$_2$CH$_2$CH$_2$CH$_2$CH$_2$NH$_2$, —CH$_2$CH$_2$CH$_2$CH$_2$CH$_2$CH$_2$NH$_2$, —CH$_2$CH$_2$NHCH$_3$, —CH$_2$CH$_2$CH$_2$NHCH$_3$, —CH$_2$(CH$_3$)CHCH$_2$NHCH$_3$, —CH$_2$CH$_2$CH$_2$CH$_2$NHCH$_3$, —CH$_2$CH$_2$NHCH$_2$CH$_2$NH$_2$, —CH$_2$CH$_2$CH$_2$NHCH$_2$CH$_2$CH$_2$NH$_2$, —CH$_2$CH$_2$CH$_2$CH$_2$NHCH$_2$CH$_2$CH$_2$NH$_2$, —CH$_2$CH$_2$NHCH$_2$CH$_2$NHCH$_3$, —CH$_2$CH$_2$CH$_2$NHCH$_2$CH$_2$CH$_2$NHCH$_3$, —CH$_2$CH$_2$CH$_2$CH$_2$NHCH$_2$CH$_2$CH$_2$CH$_2$NHCH$_3$, and —CH$_2$CH$_2$NHCH$_2$CH$_2$NHCH$_2$CH$_2$CH$_3$. Typically, the amino functional group is —CH$_2$CH$_2$CH$_2$NH$_2$ or —CH$_2$CH(CH$_3$)CH$_2$NH(CH$_3$).

The amino terminated polydiorganosiloxanes are further illustrated by polydimethylsiloxanes fluids terminated with an amino functional hydrocarbon group. Typically, the viscosity at 25° C. of the amino terminated polydimethylsiloxane fluids ranges from 10 to 100,000 mm$^2$/s (centistokes, cS), or alternatively from 10 to 1,000 mm$^2$/s (centistokes, cS).

Representative, non-limiting examples of amino terminated polydiorganosiloxanes that can be used in the present invention are;

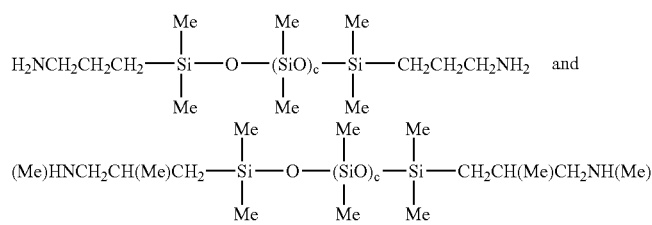

wherein c ranges from 1 to 1000, alternatively 1 to 500, or alternatively, 1 to 200.

Representative, non-limiting examples of commercially available amino terminated polydiorganosiloxanes that can be used in the present invention are Dow Corning® 2-8577 (Dow Corning Corporation, Midland, Mich.), and BY 16-853U (Dow Corning Toray Silicones, Chiba, Japan).

The compositions of the present invention are prepared by combining components A) and B) using any conventional mixing techniques. Components A) and B) can be combined either before addition to a finishing bath or by adding them separately into the finishing bath. Typically, components A) and B) are mixed such that the weight ratio of component A)/component B) is from 1/99 to 99/1, alternatively from 5/95 to 95/5.

The invention further provides a method of treating fibers or textiles comprising;
I) mixing,
A) a fluoropolymer,
B) an amino terminated polydiorganosiloxane, and
II) applying the product of step I on fibers or textiles.

The first step of the method is mixing a fluoropolymer and an amino terminated polydiorganosiloxane. The fluoropolymer A) and the amino terminated polydiorganosiloxane B) are the same as described supra, and the quantities used are as described supra. Components A) and B) can be combined either before addition to a finishing bath or by adding them separately into the finishing bath. Mixing can be performed by any conventional known techniques such as milling, blending, homogenizing, sonolating or stirring. These mixing procedures can be conducted either in a batch or continuous process.

The second step of the method comprises applying to fibers or textiles the product resulting from mixing components A) and B), i.e. the product of step I), also referred herein as the treatment composition. The amount applied is a "hand improving" effective amount of the treatment composition and is applied to the fiber and/or textile by any convenient method. For example, the treatment composition can be applied by padding, dipping, spraying or exhausting. When the treatment composition comprises more than one solution, dispersion, or emulsion; the solutions, dispersions, and emulsions can be applied simultaneously or sequentially to the textiles. After the treatment composition is applied to the fiber and/or fabric, it can be dried by heat.

The fiber/textile treatment composition can be applied to the fiber and/or textile during making the fibers or textiles, or later such as during laundering textiles. After application, carriers (if any) can be removed from the treatment composition for example by drying the composition at ambient or elevated temperature. The amount of treatment composition applied to the fibers and textiles is typically sufficient to provide 0.1 to 15 weight percent of the composition on the fibers and textiles, based on their dry weight, preferably in an amount of 0.2 to 5 weight percent based on the dry weight of the fiber or textile.

Additional components, such as other treatment agents and finishing chemicals known in the art, can be added to the treatment process. For example, the finishing bath may also include additional components such as, but not limited to, durable press reactants, such as dimethyloldihydroxyethylene urea (DMDHEU), reactant catalysts such as magnesium chloride/citric acid, softeners such as polyethylene emulsions, process aids such as wetting agents and other.

Fibers and textiles that can be treated with the treatment composition include natural fibers such as cotton, silk, linen, and wool; regenerated fibers such as rayon and acetate; synthetic fibers such as polyesters, polyamides, polyacrylonitriles, polyethylenes, and polypropylenes; combinations, and blends thereof. The form of the fibers can include threads, filaments, tows, yarns, woven fabrics, knitted materials, non-woven materials, paper, carpet, and leather.

The treatment composition of this invention has advantages such that it can impart combined benefits of attributes associated with silicones and fluorocarbons. Silicones generally provide superior hand to fabrics, whereas fluorocarbons contribute water repellency, oil repellency, and soil release to textiles. Hand for purposes of the invention means the softness and smoothness of the fabric. The present compositions and methods provide oil repellency properties to fibers or textiles, but without a significant detriment to the hand of treated fibers.

EXAMPLES

The following examples are presented to further illustrate the compositions and methods of this invention, but are not to be construed as limiting the invention, which is delineated in the appended claims. All parts and percentages in the examples are on a weight basis and all measurements were obtained at about 23° C., unless indicated to the contrary.

Treatment of Textiles and Test Methods

Fabrics were obtained from Testfabrics Incorporated, Pittston, Pa., and included a 100 percent cotton twill Tribecka series khaki, and a No. 7409 Dacron, 54 weight/Cotton, 65/35 Bleached Broadcloth and Interlock cotton knit style 460, as the standardized fabrics for use. Neither fabric had any pre-finished treatment.

Oil Repellency: Hydrocarbon Resistance Test Protocol—American Association of Textile Chemists & Colorists (AATCC) Test Method 118-1997

In this test method, a series of oils are designated with numbers 1 thru 8. The surface tension of the oil decreases as the number of the oil increases, i.e., the number 1 oil has the highest surface tension, whereas the number 8 oil has a lowest surface tension. Each fabric is tested with the number oil (Kaydol) up to the number 8 oil (n-heptane), and the wetting or wicking into the fabric is noted. Values based on a rating scale of A, B, C, and D, are assigned to each oil as an indication of the contact angle of the oil applied to the surface, and at a C value, wicking and wetting of the fabric is noted, with full wicking being a rating of D. Value A is the best, value B is passing, value C indicates failure, and value D is the worst. The test protocol consists of placing 5 drops of each oil on the test fabric, waiting 30+/-2 seconds, and then assigning a score for the oil. If the score is B or better, the next higher numbered oil is tested. A score of 8A is considered the best score since it would indicate that there was no or little if any wicking and/or wetting of the fabric even with the oil having the lowest surface tension.

Water Repellency: Spray Test—AA TCC Test Method 22-1996

An AATCC spray tester was used for this test. The tester included a stand with a 45° incline, above which a separatory funnel was mounted having an attached spray nozzle hanging above it. Fabric samples are fastened into a metal hoop, and placed on the incline, and the nozzle head is positioned 6 inches above it. Then, 250 milliliter of distilled water is allowed to play down onto the fabric. The wetting pattern is compared to a standard rating scale. A rating of 100 indicates no sticking or wetting of the upper surface; a rating of 90 indicates a slight random sticking or wetting of the upper surface; a rating of 80 indicates a wetting of the upper surface at the spray points; a rating of 70 indicates a partial wetting of the whole of upper surface; a rating of 50 indicates a complete wetting of the whole of the upper surface; a rating of 0 indicates a complete wetting of the whole of the upper and lower surfaces.

Water/IPA Drop Test

This method was used to evaluate the water repellency of the interlock cotton knit. In this method, solutions with ratios of water and isopropyl alcohol (IPA) from 100:0 to 0:100 are prepared, and 5 drops of each solution are placed on the surface to observe whether penetration occurs within 10 seconds. The higher the ratio of IPA in the solution, the lower the surface tension, the more difficult to repel and therefore the higher rating given, e.g. a fabric repelling 100% IPA was given a rating of 100.

Hand Testing

A panel of expert evaluators rated the fabric softness using a scale of 1 to 5. A value of 5 was used for the softest fabric and a value of 1 was given to the least soft fabric.

Finishing Procedure

Three different fluoropolymer emulsions were used in the design of the finishing formulations. Three emulsions were compositions containing a fluoroalkyl acrylate copolymers, and the other emulsion was a composition containing a fluorinated urethane. The emulsions containing the fluoroalkyl acrylate copolymers were obtained from Noveon Corporation, sold as Unydine® TG-532 and Daikin Industries, sold as Unydine® 571. All compositions are known to provide good stain repellency and/or stain release to textile substrates made of all types of fibers and fiber blends. The required amount of the emulsion components was added to the water-finishing bath in order to deposit the specified amount of solids on fabric. Swatches of test fabric were cut from single bolts of fabric into square measuring 15"×15".

Finishing bath was applied to the fabric by padding where it is impregnated with the bath liquor followed by squeezing through a nip to leave a specific quantity of liquor on the substrate. After padded, the fabric was dried and cured in a laboratory stenter at 170° C., for 90 sec.

Materials

The following materials were used in the examples, as detailed below.

Amino-terminated I=Dow Corning® 2-8577, an amino terminated polydimethylsiloxane (Dow Corning Corporation, Midland, Mich.)

Amino-terminated II=BY16-853U, an amino terminated polydimethylsiloxane (Dow Corning Toray Silicones, Chiba, Japan)

Microemulsions of each were prepared and applied in a stain repellent and release fabric finish formulations to different fabric substrates. The representative finishing systems were based on either fluoroalkyl acrylate copolymers or a fluorinated urethanes.

Example 1

Fluorocarbon System I: Noveon's Unidyne TG-532 System(I)

Unidyne TG-532 is a fluoroalkyl acrylate copolymer emulsion (19% actives, 25% solids). The oil repellency results of amino-terminated silicones in the Unidyne TG-532 are summarized in the table below. Results are compared to those obtained with amino terminated silicones I and II and Dow Corning SM8715EX, epoxyfunctional silicone emulsions (commonly used in this application) and to a conventional grafted aminofunctional silicone, Dow Corning 2-8040. Results are summarized below.

1.1 100% Cotton Knit, 1.4% Silicone and 1.5% Fluoropolymer Based on Weight of Fabric (OWF)

| Oil Repellency (Hydrocarbon Resistance Test-AATCC 118-1992) | | | | | | | |
|---|---|---|---|---|---|---|---|
| Treatment/Oil | 7 | 6 | 5 | 4 | 3 | 2 | 1 |
| Unidyne TG-532 Only | A– | A | A | A | A | A | A |
| Unidyne TG-532 & Aminoterminated I | B | A– | A | A | A | A | A |

-continued

| | | | | | | | |
|---|---|---|---|---|---|---|---|
| Unidyne TG-532 & Epoxysilicone | C | B | A– | A | A | A | A |

Water Repellency, Spray Rating (AATCC-22)

| Treatment | Unidyne TG-532 Only | Unidyne TG-532 & 2-8577 | Unidyne TG-532 & SM-8715 |
|---|---|---|---|
| Rating | 85 | 80 | 80 |

-continued

Hand Rating

| Treatment | Unidyne TG-532 Only | Unidyne TG-532 Amino terminated | Unidyne TG-532 & Epoxysilicone |
|---|---|---|---|
| Series 1 | 1 | 4 | 5 |

(1) Relative Hand Rating obtained from a panel of expert evaluators: 1 is the least soft, 5 is the softest.

1.2 Polycotton (65/35), 1% Silicone, 1% Fluoropolymer (OWF)

Oil Repellency (Hydrocarbon Resistance Test-AATCC 118-1992)

| Treatment/Oil | 7 | 6 | 5 | 4 | 3 | 2 | 1 |
|---|---|---|---|---|---|---|---|
| Unidyne TG-532 Only | B– | B | A– | A | A | A | A |
| Unidyne TG-532 & Amino Terminated II | B– | B– | B | A– | A | A | A |
| Unidyne TG-532 & Amino-terminated I | B– | B– | B | A– | A | A | A |
| Unidyne TG-532 & Epoxysilicone | B– | B– | B | A– | A | A | A |
| Unidyne TG-532 & Conventional Amino | C | C | C | B– | B– | A– | A |

Water Repellency, Spray Rating (AATCC-22)

| Treatment | Unidyne TG-532 Only | Unidyne TG-532 & Amino Terminated I | Unidyne TG-532 & Amino Terminated II | Unidyne TG-532 & Epoxysilicone | Unidyne TG-532 & Conventional Amino |
|---|---|---|---|---|---|
| Rating | 100 | 95–100 | 80 | 100 | 80 |

Hand Rating

| Treatment | Unidyne TG-532 Only | Unidyne TG-532 & Amino Terminated I | Unidyne TG-532 & Amino Terminated II | Unidyne TG-532 & Epoxysilicone | Unidyne TG-532 & Conventional Amino |
|---|---|---|---|---|---|
| Series 1 | 1 | 3.4 | 3 | 3.5 | 5 |

(1) Relative Hand Rating obtained from a panel of expert evaluators: 1 is the least soft, 5 is the softest.

Example 2

Fluorocarbon System II: Noveon's Unidyne TG-571 System(1)

Unidyne TG-571 is a fluoroalkyl acrylate copolymer emulsion (30% actives, 40% solids). The oil repellency results of amino-terminated silicones in the Unidyne TG-571 are summarized in the table below. Results are compared to those obtained with SM8715EX, an epoxy-functional silicone emulsion, which is the standard silicone softener used in this application and also against 2-8040, a conventional grafted aminofunctional silicone.

2.1 Cotton Khaki Twill, 1% Silicone, 1% Fluoropolymer (OWF)

Oil Repellency (Hydrocarbon Resistance Test-AATCC 118-1992)

| Treatment/Oil | 7 | 6 | 5 | 4 | 3 | 2 | 1 |
|---|---|---|---|---|---|---|---|
| Unidyne TG-571 Only | — | C | B | A– | A | A | A |

-continued

| | | | | | | | |
|---|---|---|---|---|---|---|---|
| Unidyne TG-571 & Amino Terminated I | B- | B | A- | A- | A | A | A |
| Unidyne TG-571 & Epoxy Silicone | — | C | B | B | A- | A | A |
| Unidyne TG-571 & Conventional Amino | — | C | C | B | A- | A | A |

Water Repellency, Spray Rating (AATCC-22)

| Treatment | Unidyne TG-571 Only | Unidyne TG-571 & AminoTerminated I | Unidyne TG-571 Epoxysilicone | Unidyne TG-571 Conventional Amino |
|---|---|---|---|---|
| Rating | 95 | 90 | 100 | 85 |

Hand Rating

| Treatment | Unidyne TG-571 Only | Unidyne TG-571 & AminoTerminated | Unidyne TG-571 & Epoxysilicone | Unidyne TG-571 Conventional Amino |
|---|---|---|---|---|
| Series 1 | 1 | 4.5 | 3.75 | 5 |

(1) Relative Hand Rating obtained from a panel of expert evaluators: 1 is the least soft, 5 is the softest.

2.2 Cotton Khaki Twill, 0.5% Silicone, 1% Fluoropolymer (owf)

Oil Repellency (Hydrocarbon Resistance Test-AATCC 118-1992)

| Treatment/Oil | 7 | 6 | 5 | 4 | 3 | 2 | 1 |
|---|---|---|---|---|---|---|---|
| Unidyne TG-571 Only | — | C | B- | B | A | A | A |
| Unidyne TG-571 & Amino Terminated I | B- | B- | B | B | A- | A | A |
| Unidyne TG-571 & Epoxy Silicone | — | C | B- | B | A- | A | A |
| Unidyne TG-571 & Conventional Amino | | | C | B | A- | A | A |

Water Repellency, Spray Rating (AATCC-22)

| Treatment | Unidyne TG-571 Only | Unidyne TG-571 & Amino Terminated I | Unidyne TG-571 Epoxysilicone | Unidyne TG-571 Conventional Amino |
|---|---|---|---|---|
| Rating | 95 | 100 | 100 | 85 |

Hand Rating

| Treatment | Unidyne TG-571 Only | Unidyne TG-571 & Amino Terminated I | Unidyne TG-571 Epoxysilicone | Unidyne TG-571 Conventional Amino |
|---|---|---|---|---|
| Series 1 | 1 | 4 | 5 | 3.5 |

(1) Relative Hand Rating obtained from a panel of expert evaluators: 1 is the least soft, 5 is the softest.

2.3 100% Cotton Knit, 1.4% Silicone, 1.3% Fluoropolymer (owf)

| Oil Repellency (Hydrocarbon Resistance Test-AATCC 118-1992) | | | | | | | |
|---|---|---|---|---|---|---|---|
| Treatment/Oil | 7 | 6 | 5 | 4 | 3 | 2 | 1 |
| Unidyne TG-571 Only | | | B | B | A– | A | A |
| Unidyne TG-571 & Amino Terminated I | B– | B– | B | B | A– | A | A |
| Unidyne TG-571 & Epoxy Silicone | | | C+ | B– | B– | B | A |
| Unidyne TG-571 & Conventional Amino | | | B | B | A– | A | A |

| | Water Repellency, Water/IPA Drop absorbency Test | | | |
|---|---|---|---|---|
| Treatment | Unidyne TG-532 Only | Unidyne TG-532 & AminoTerminated I | Unidyne TG-571 Epoxysilicone | Unidyne TG-571 Conventional Aminosilicone |
| Rating | 50 | 50 | 60 | 20 |

| | Hand Rating | | | |
|---|---|---|---|---|
| Treatment | Unidyne TG-571 Only | Unidyne TG-571 & AminoTerminated I | Unidyne TG-571 Epoxysilicone | Unidyne TG-571 Conventional Aminosilicone |
| Series 1 | 1 | 4 | 4.3 | 4.5 |

(1) Relative Hand Rating obtained from a panel of expert evaluators: 1 is the least soft, 5 is the softest.

2.4 100% Cotton Knit, 0.7% Silicone, 1.3% Fluoropolymer (owf)

| Oil Repellency (Hydrocarbon Resistance Test-AATCC 118-1992) | | | | | | | |
|---|---|---|---|---|---|---|---|
| Treatment/Oil | 7 | 6 | 5 | 4 | 3 | 2 | 1 |
| Unidyne TG-571 Only | — | C | B | B+ | A– | A | A |
| Unidyne TG-571 & Amino Terminated I | — | C | B | B+ | A– | A | A |
| Unidyne TG-571 & Epoxy Silicone | — | — | B– | B | B | A– | A |
| Unidyne TG-571 & Conventional Amino | — | — | C | B+ | A– | A | A |

| | Water Repellency, Water/IPA Drop absorbency Test | | | |
|---|---|---|---|---|
| Treatment | Unidyne TG-532 Only | Unidyne TG-532 & AminoTerminated I | Unidyne TG-571 Epoxysilicone | Unidyne TG-571 Conventional Aminosilicone |
| Rating | 50 | 50 | 60 | 30 |

| | Hand Rating | | | |
|---|---|---|---|---|
| Treatment | Unidyne TG-571 Only | Unidyne TG-571 & AminoTerminated I | Unidyne TG-571 Epoxysilicone | Unidyne TG-571 Conventional Aminosilicone |
| Series 1 | 1 | 4.5 | 5 | 4 |

(1) Relative Hand Rating obtained from a panel of expert evaluators: 1 is the least soft, 5 is the softest.

2.5 Polycotton (65/35), 1% Silicone, 1% Fluoropolymer

| Oil Repellency (Hydrocarbon Resistance Test-AATCC 118-1992) | | | | | | | |
|---|---|---|---|---|---|---|---|
| Treatment/Oil | 7 | 6 | 5 | 4 | 3 | 2 | 1 |
| Unidyne TG-571 Only | B− | B− | B− | B− | B | B+ | B+ |
| Unidyne TG-571 & Amino Terminated I | B− | B− | B− | B− | B− | B | B |
| Unidyne TG-571 & Epoxy Silicone | B− | B− | B− | B− | B− | B | B |
| Unidyne TG-571 & Conventional Amino | | | C+ | B− | B− | B | B+ |

| | Water Repellency, Spray Rating (AATCC-22) | | | |
|---|---|---|---|---|
| Treatment | Unidyne TG-571 Only | Unidyne TG-571 & AminoTerminated I | Unidyne TG-571 Epoxysilicone | Unidyne TG-571 Conventional Amino |
| Rating | 100 | 95 | 100 | 80 |

| | Hand Rating | | | |
|---|---|---|---|---|
| Treatment | Unidyne TG-571 Only | Unidyne TG-571 & AminoTerminated I | Unidyne TG-571 Epoxysilicone | Unidyne TG-571 Conventional Amino |
| Series 1 | 1 | 4 | 4.5 | 4.5 |

(1) Relative Hand Rating obtained from a panel of expert evaluators: 1 is the least soft, 5 is the softest.

The invention claimed is:

1. A fabric treatment composition comprising;
A) a fluoropolymer,
B) an amino terminated polydiorganosiloxane,
wherein the amino terminated polydiorganosiloxane has the formula $A\text{-}(R_2SiO)_c\text{-}A$, where A is an amino-functional hydrocarbon group, R is an alkyl or aryl group, and c is greater than zero.

2. The composition according to claim 1 where R is methyl.

3. The composition according to claim 1 where c is 1–200.

4. The composition according to claim 1 where A is $CH_2CH_2CH_2NH_2$ or $CH_2CH(CH_3)CH_2NH(CH_3)$.

5. A method of treating fibers or textiles comprising;
I) mixing,
A) a fluoropolymer,
B) an amino terminated polydiorganosiloxane, and
II) applying the mixture of step I on fibers or textiles,
wherein the amino terminated polydiorganosiloxane has the formula $A\text{-}(R_2SiO)_c\text{-}A$, where A is an amino-functional hydrocarbon group. R is an alkyl or aryl group, and c is greater than zero.

6. A fiber or textile prepared by the treatment method of claim 5.

* * * * *